United States Patent [19]

Swearingen

[11] Patent Number: 4,805,619
[45] Date of Patent: Feb. 21, 1989

[54] THERAPEUTIC COOLING SCARF, WRAP OR COLLAR

[76] Inventor: David W. Swearingen, 3502 E. Ludlow Dr., Phoenix, Ariz. 85032

[21] Appl. No.: 75,437

[22] Filed: Jul. 20, 1987

[51] Int. Cl.⁴ .......................... A61N 3/00; A61F 7/00
[52] U.S. Cl. .................................. 128/380; 128/402; 383/901
[58] Field of Search ................. 62/50, 259.3; 128/399, 128/402, 403, 379, 380; 383/401; 2/207, 129

[56] References Cited

U.S. PATENT DOCUMENTS

| | | | |
|---|---|---|---|
| 1,567,931 | 12/1925 | Epler . | |
| 1,616,961 | 2/1927 | Carter . | |
| 1,910,328 | 5/1933 | Glennan | 128/402 |
| 1,927,751 | 9/1933 | Menji | 128/403 |
| 2,071,706 | 2/1937 | Reach | 128/403 |
| 2,339,409 | 1/1944 | Joy et al. | 128/379 |
| 3,074,250 | 1/1963 | Everett | 128/403 |
| 3,678,936 | 7/1972 | McCormick | 128/402 |
| 3,748,661 | 7/1973 | Smith | 2/207 |
| 3,839,621 | 10/1974 | Hairu | 128/380 |
| 3,889,684 | 6/1975 | Lebold | 128/402 |
| 4,061,897 | 12/1977 | Thykeson | 128/379 |
| 4,204,543 | 5/1980 | Henderson | 128/403 |
| 4,356,709 | 11/1982 | Alexander | 62/530 |
| 4,576,169 | 3/1986 | Williams | 128/402 |
| 4,641,655 | 2/1987 | Abt | 128/380 |
| 4,645,498 | 2/1987 | Kosak | 128/403 |

FOREIGN PATENT DOCUMENTS

| | | | |
|---|---|---|---|
| 718686 | 9/1965 | Canada | 128/380 |
| 014300 | 8/1980 | European Pat. Off. | 128/402 |

Primary Examiner—Richard C. Pinkham
Assistant Examiner—Mark S. Graham
Attorney, Agent, or Firm—Warren F. B. Lindsley

[57] ABSTRACT

An ice applicator in the form of an elongated scarf for wearing around the neck of a person subjected to high ambient heat conditions employing a cavity which is filled with a frozen water medium. The ends of the scarf are provided with a pair of fastening means, one for securing the ends of the scarf together in a juxtapositioned arrangement when worn, and a second one for securing the ice applicator to the chest of the wearer.

3 Claims, 1 Drawing Sheet

THERAPEUTIC COOLING SCARF, WRAP OR COLLAR

BACKGROUND OF THE INVENTION

This invention relates generally to a body cooling device and more particularly to a scarf, wrap or collar which may be worn about the neck of a person subject to high ambient heat conditions.

This scarf, wrap or collar may comprise an envelope of a porous fabric material capable of being shaped to conform to and hold itself against the contour of a body area being covered. The envelope is intended to contain ice, the melting of which will penetrate the fabric material and cool the surrounding body area while one is engaged in work, sports or other vigorous activities in a hot environment.

In some instances, the envelope may be lined with a liquid impervious material and in this instance, the wrap will transfer a dry cool temperature to the body of the wearer.

DESCRIPTION OF THE PRIOR ART

Although the beneficial effects of the application of wet and dry cold compresses to the body in hot weather have long been recognized, the uses of such compresses have generally been applied to patients lying in a bed or otherwise inactive. Those that have been designed for persons active in a vigorous activity, have not been designed for effective use.

U.S. Pat. No. 4,641,655 discloses a therapeutic cooling wrap designed for tying around the neck of a person. A bag closed by a zipper forms a pouch in a strip of pervious fabric. The strip of fabric is further stitched to form tying straps on both ends of the pouch. A pad of open-pored foam is secured in the bag to insulate the neck from severe cold still permitting the controlled dispensing of water to the neck area.

U.S. Pat. No. 4,356,709 discloses an ice cap having an inner wall and an outer wall defining a sealed cavity. The inner wall is comprised of an inner laminate of moisture impervious material and an outer laminate of textile material such as cloth. The outer wall is essentially the same.

U.S. Pat. No. 3,889,684 discloses a hot and cold pack which may be secured to the neck by a VELCRO-type fastener.

U.S. Pat. No. 3,678,936 discloses an ice bag comprising two sleeves of rubberized flannel disposed one within the other and sealed. When the zipper is opened, ice is inserted therein.

U.S. Pat. No. 4,576,169 discloses a collar to be worn around the neck for cooling. A towel member encloses an insulating member with a cooling pocket located between the insulating member and the user's neck.

U.S. Pat. Nos. 1,567,931 and 1,616,961 disclose compresses and neck bags containing ice or liquid which are of a different geometrical configuration than that disclosed herein.

Canadian Pat. No. 718,686 discloses an envelope which conforms to fit around the entire neck of a user which contains a particular filling possessing the quality of retaining heat over relatively long periods of time.

None of these patents disclose the structure claimed which is simple in design, effective in use and can be easily used by man, woman or child when out of doors in a hot environment.

SUMMARY OF THE INVENTION

In accordance with the invention claimed, a new and improved wrap around scarf or collar is disclosed which is economical to manufacture and effective when used to aid in rendering activities in a hot environment more feasible.

It is, therefore, one object of this invention to provide a new and improved elongated device such as a scarf, wrap or collar which can be comfortably worn about the neck of a person subjected to high ambient heat conditions to effectively and efficiently lower the body temperature of the wearer.

Another object of this invention is to provide a cooling scarf, wrap or collar that can receive and retain a frozen water medium and which dispenses water as the frozen water medium melts through a porous medium to the skin of the wearer.

A further object of this invention is to provide a cooling scarf, wrap or collar that receives a frozen water medium within a liquid nonpervious envelope to which body heat can be transferred.

A still further object of this invention is to provide a new and improved wrap around scarf that can be secured to the body of the user while one is engaged in sports or other vigorous activities.

A still further object of this invention is to provide a wrap around scarf which can be economically manufactured and sold at a reasonable price.

Further objects and advantages of the invention will become apparent as the following description proceeds and the features of novelty which characterize the invention will be pointed out with particularity in the claims annexed to and forming a part of this specification.

BRIEF DESCRIPTION OF THE DRAWING

The present invention may be more readily described by reference to the accompanying drawing in which.

DESCRIPTION OF THE PREFERRED EMBODIMENT

Figure 1:
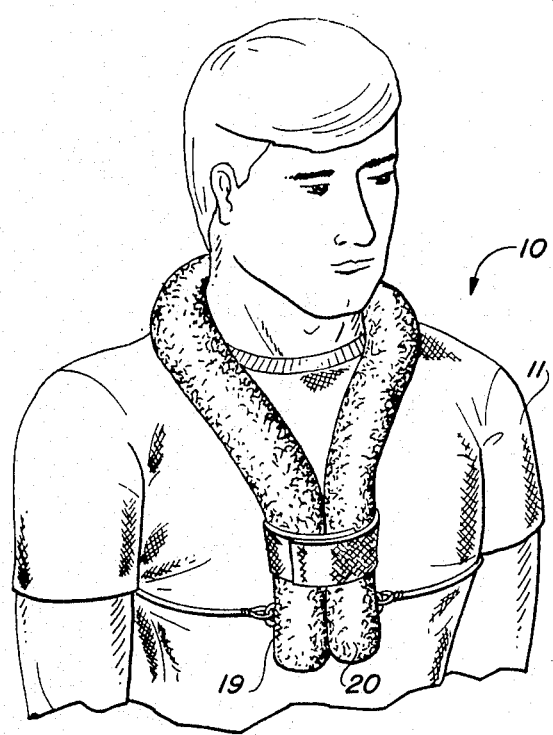
FIG. 1 illustrates the upper half of a user with a cooling scarf embodying the invention wrapped around his neck.
Figure 2:
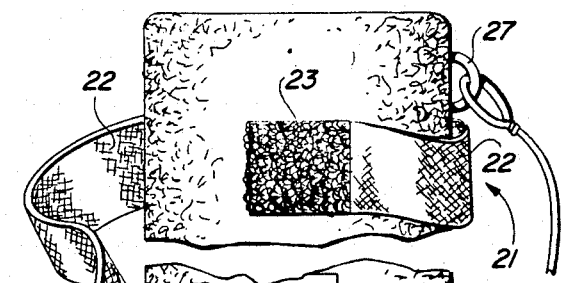
FIG. 2 is an elongated view of the scarf shown in FIG. 1.
Figure 2:
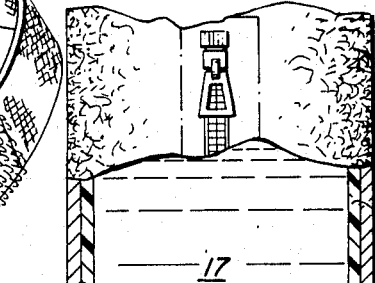
Figure 2:
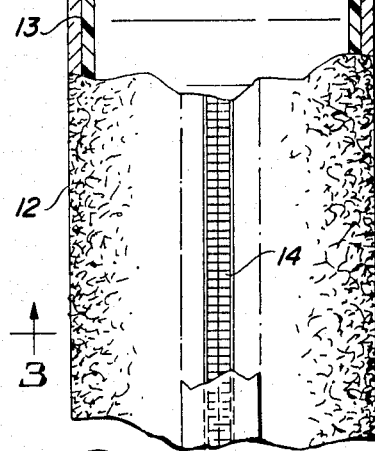
Figure 2:
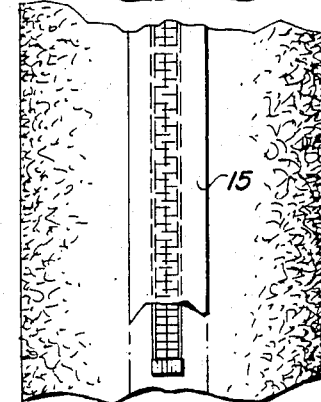
Figure 3:
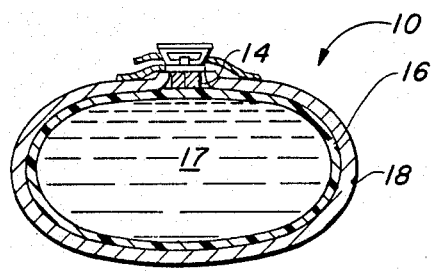
FIG. 3 is a cross-sectional view of FIG. 2 taken along the line 3—3.

Referring more particularly to the drawing by characters of reference, FIGS. 1–3 disclose an elongated cooling ice applicator, scarf, wrap or collar 10 for tying around the neck of a wearer 11. This scarf, as shown in FIG. 2, comprises an elongated hollow cylindrical-like member formed of an absorbent textile material, the interior of which forms an envelope 12, the cavity of which may be filled directly with ice or with one or more containers filled with a freezable medium.

Although the scarf or cooling wrap may be used as a cold compress for application to another part of the body, it is especially intended to be worn, as shown in FIG. 1, around the neck when the user is engaged in vigorous activity such as playing tennis, performing physical labor or exercising and the like. The removal of heat from the neck area, as is well known, will give relief from some of the symptoms associated with being overheated. Heat is removed from the neck area by scarf, wrap or collar 10 by conduction and/or the dispensing by it of a controlled amount of water on the neck which absorbs the heat through evaporation.

As noted from FIG. 2, the configuration of cooling scarf, wrap or collar 10 comprises an elongated single strip of fabric such as an absorbent toweling material which is folded back on itself and stitched in an overlapping manner to form a hollow interior 13 which is opened and closed by zipper means 14 which is covered by an overlapping edge 15 of the material. Zipper means 14 is shown as extending along only a part of the length of scarf 10 midway of its length.

The fabric strip used to form the cooling wrap may be approximately 36 inches long, 9 inches wide and when folded over on itself from end to end and stitched, forms an envelope with a 7 inch circumference with a flap or overlapping edge 15 of approximately 2 inches covering the zipper means 14.

As shown in FIGS. 2 and 3, the interior of envelope 12 is lined with a liquid impervious material 16 to form a lining or bag for the scarf or it may be periodically supplied with one or more containers containing a freezable medium 17 as hereinafter described, which may be repeatedly used and refrozen.

Since the scarf is formed of a toweling material 18, the use of the scarf shown in FIGS. 1–3 will cool the user by conduction.

Figure 4:
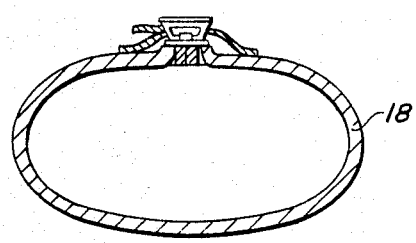
FIG. 4 is a cross-sectional view of a modification of the scarf shown in FIGS. 1–3.

FIG. 4 illustrates a modification of the scarf shown in FIGS. 1–3 wherein the scarf is formed as shown and described for FIGS. 1–3, but differs therefrom by omitting the lining shown therein. In this illustration, the toweling material 18 will become saturated by melting ice, i.e. ice cubes or crushed ice, forming the freezable medium 17 placed in envelope 11. As the ice cubes melt, the water released is immediately transferred to the toweling material 18 of the cooling scarf, and then to the neck area of the user. This water is gradually released as evaporation occurs from the cooling scarf and the neck and chest area of the wearer.

Once the frozen water medium is placed in envelope 12 of the scarf whether or not it contains a liquid nonimpervious lining and the envelope is closed by zipper means 14 and placed around the neck of a wearer, as shown in FIG. 1, the opposite ends 19 and 20 of the scarf are brought together and held in a juxtapositioned side-by-side arrangement by a fastening means 21.

This fastening means comprises a strap 22 with the ends of the strap each being provided with one portion 23 of a VELCRO (hook and loop) fastener member and the corresponding area of the other end of the strap being provided with a cooperating VELCRO member 24.

This fastening means is provided for easy clamping together of the ends of the scarf around the neck of the wearer and removable therefrom.

A further fastening means 25 is provided for securing the scarf around the chest of the wearer so as to prevent the scarf from flopping around when used by one involved in a vigorous activity such as running.

This fastening means comprises a pair of clamps 26 and 27, one fastened on each of the opposite ends of the scarf and on a common side thereof as shown in FIG. 2. A strap 28 with suitable adjustment means for varying the end of the strap is provided for engaging clamps 26 and 27 to hold the ends of the scarf against the chest of the wearer in a known manner.

Figure 5:
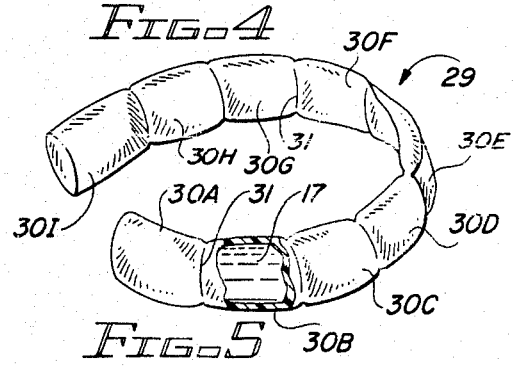
FIG. 5 is a perspective view partly broken away of a frozen medium enclosing insert for insertion in the hollow cavity of the structure shown in FIGS. 1–3.

FIG. 5 discloses one form of a container 29 which may be used for insertion into envelope 12 to form the freezable medium 17.

In this instance, container 29 comprises a plurality of interconnected but separated pouches 30A–30I, each formed with a liquid nonpervious surface which are interconnected in the sequential arrangement shown by a necked down web 31 between each of the pouches. These webs each form a hinge permitting container 29 to form a straight line or arcuate configuration depending on the configuration of the scarf when in use or stored.

This container may be repeatably used after each freezing cycle.

Although but a few embodiments of the invention have been shown and described, it will be apparent to those skilled in the art that various changes and modifications may be made therein without departing from the spirit of the invention or from the scope of the appended claims.

What is claimed is:

1. An ice applicator for wearing around the neck of a person subjected to high ambient heat conditions comprising:
    an elongated member having two ends and formed of a water absorbent textile material,
    said member having an elongated cavity formed therein closed by a zipper means,
    said member being adaptable to substantially encompass and form a scarf around the neck of a wearer when placed therearound with said ends meeting in a juxtapositioned side-by-side arrangement,
    a first fastening means mounted on one of said ends of said member for detachably surrounding and holding said ends together in said juxtapositioned side-by-side arrangement,
    said first fastening means comprising a strap with one end of said strap being provided with one portion of a hook and loop fastener and the other end of said strap being provided with a cooperating hook and loop fastener, and
    a second fastening means mounted on said ends of said member for detachably surrounding the chest of the wearer to hold said ends against the chest to secure said member in place during physical activity of the wearer.

2. The ice applicator set forth in claim 1 wherein:
    said cavity is lined with a liquid impervious material.

3. The ice applicator set forth in claim 1 in further combination with:
    a liquid nonpervious container containing a freezable liquid medium positioned within said cavity.

* * * * *